US012638415B2

(12) United States Patent (10) Patent No.: US 12,638,415 B2
Maki et al. (45) Date of Patent: May 26, 2026

(54) GAS SENSOR AND CASING FOR CONTAINING SENSOR ELEMENT

(71) Applicant: NGK INSULATORS, LTD., Nagoya (JP)

(72) Inventors: Shintaro Maki, Taketoyo-cho (JP); Kota Katagiri, Ginan-cho (JP); Kohei Yaita, Nagoya (JP); Takaaki Ishii, Kasugai (JP); Yuya Seike, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 314 days.

(21) Appl. No.: 18/185,579

(22) Filed: Mar. 17, 2023

(65) Prior Publication Data

US 2023/0314364 A1      Oct. 5, 2023

(30) Foreign Application Priority Data

Mar. 31, 2022    (JP) ................................. 2022-058995

(51) Int. Cl.
G01N 27/407 (2006.01)
G01N 27/406 (2006.01)
(Continued)

(52) U.S. Cl.
CPC ..... G01N 27/4078 (2013.01); G01N 27/4062 (2013.01); G01N 27/4067 (2013.01);
(Continued)

(58) Field of Classification Search
CPC ........... G01N 27/4077; G01N 27/4062; G01N 27/4078; G01N 27/26; G01N 27/403; G01N 27/406; G01N 27/407
See application file for complete search history.

(56) References Cited

U.S. PATENT DOCUMENTS 7,234,341 B2 *    6/2007    Nishio ................. G01N 27/407
                                                73/23.31
2006/0272944 A1 *  12/2006   Ichiyanagi ......... G01N 27/4078
                                                204/424

FOREIGN PATENT DOCUMENTS

JP            2015-227790 A      12/2015
JP            2019-15524 A        1/2019
JP            6787810 B2         11/2020

OTHER PUBLICATIONS

Japanese Office Action received in corresponding Japanese Application No. 2022-058995 dated Jul. 22, 2025.

* cited by examiner

*Primary Examiner* — Gurpreet Kaur
(74) *Attorney, Agent, or Firm* — MATTINGLY & MALUR, PC

(57) ABSTRACT

A gas sensor includes: a sensor element including a sensing part on one end portion thereof; a casing; and a connector disposed in the casing to electrically connect the sensor element to an outside, wherein the casing includes: an outer tube including a main portion in which a reference gas is included and a sealing portion with a diameter smaller than the main portion so that another end portion of the sensor element protrudes to the main portion; a rubber seal member fitted into the sealing portion; and a spacer intervening between the seal member and the connector, and the spacer is secured by being sandwiched between the connector and the seal member due to friction force acting on a contact surface with the seal member which occurs by that load acts on the spacer from the seal member in accordance with reduction in the diameter by swaging.

15 Claims, 3 Drawing Sheets

(51) Int. Cl.
     *G01N 27/41*          (2006.01)
     *G01N 33/00*          (2006.01)
(52) U.S. Cl.
     CPC ..... *G01N 27/4071* (2013.01); *G01N 27/4077*
                (2013.01); *G01N 27/41* (2013.01); *G01N*
                                 *33/0037* (2013.01)

F I G.  2
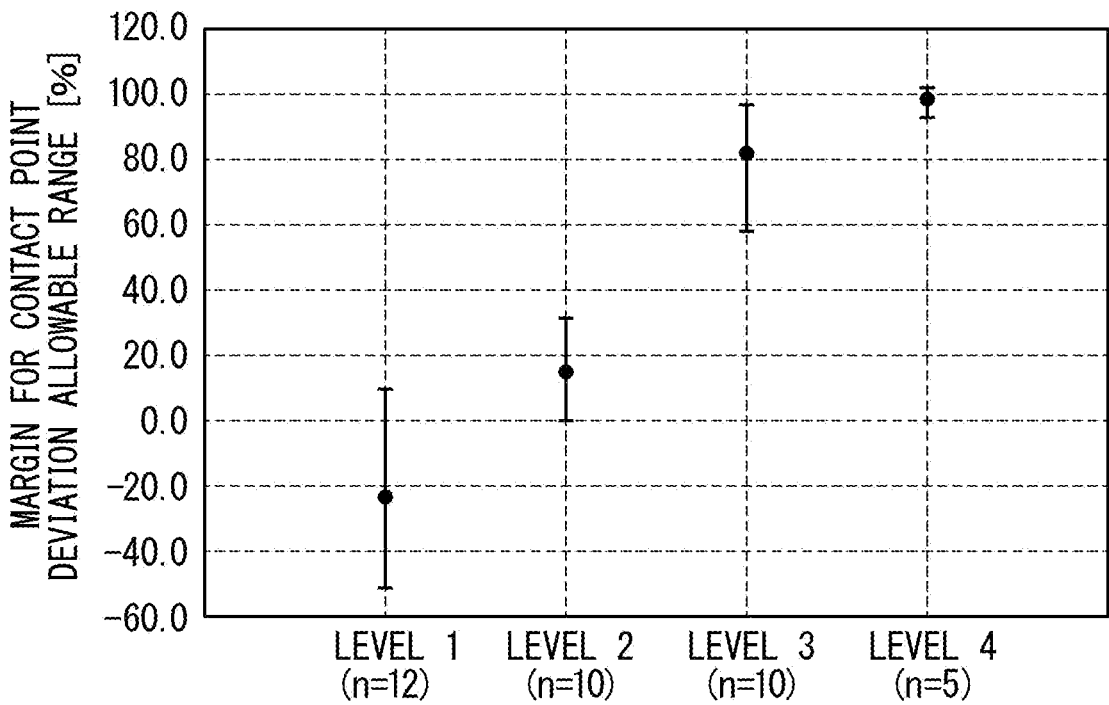

F I G. 3
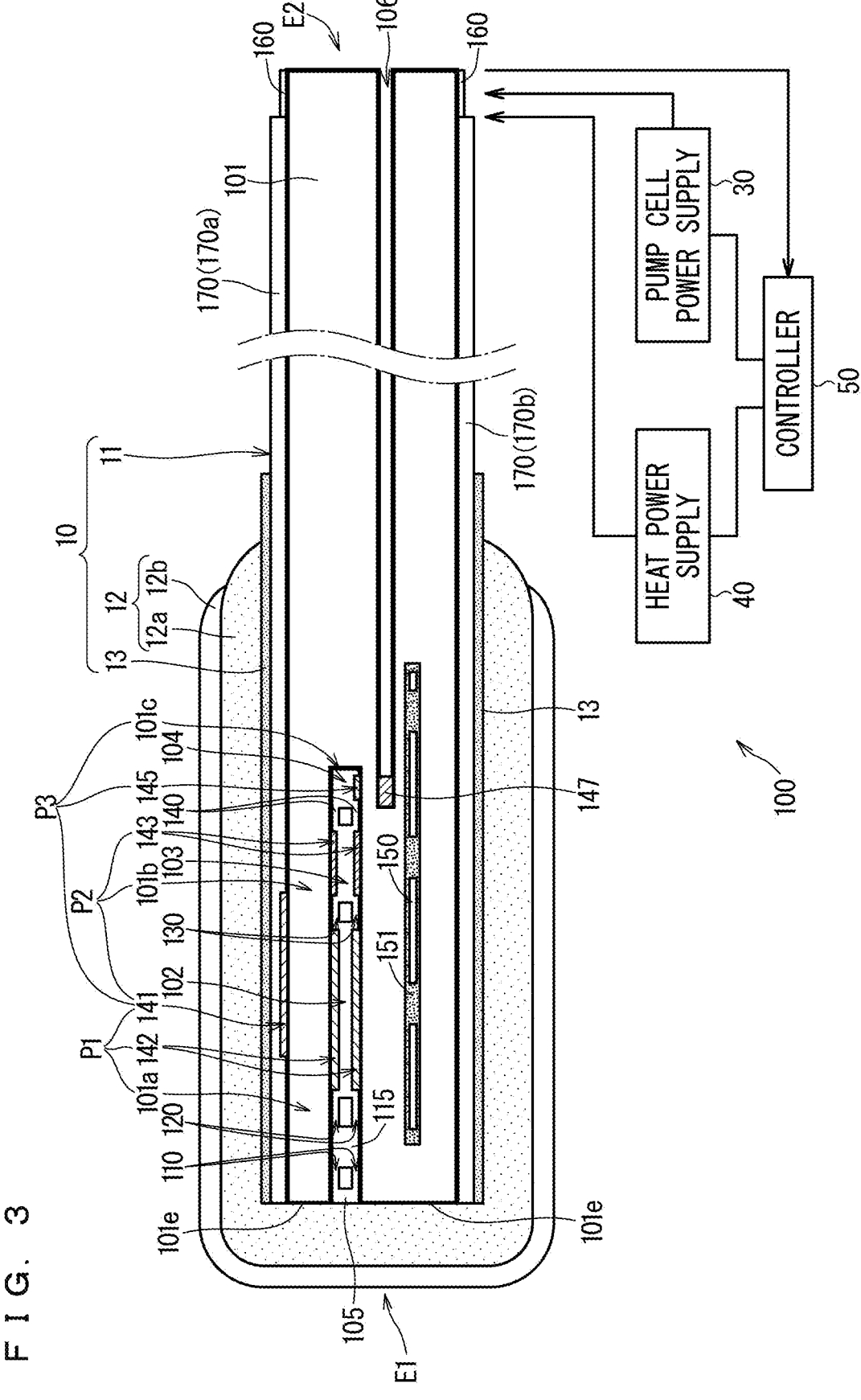

GAS SENSOR AND CASING FOR CONTAINING SENSOR ELEMENT

CROSS-REFERENCE TO RELATED APPLICATION

The present application claims priority from Japanese application JP2022-058995, filed on Mar. 31, 2022, the contents of which is hereby incorporated by reference into this application.

BACKGROUND OF THE INVENTION

Field of the Invention

The present invention relates to a gas sensor and, in particular, to securing of a spacer disposed in a casing for containing a sensor element.

Description of the Background Art

As a device for measuring a concentration of a predetermined gas component in a measurement gas, such as a combustion gas and an exhaust gas from an internal combustion engine typified by an engine of a vehicle, a gas sensor including a sensor element formed of oxygen-ion conductive solid electrolyte ceramics, such as zirconia ($ZrO_2$), has been conventionally known.

As the gas sensor, a gas sensor having a configuration in which an elongated planar sensor element (detection element) including oxygen-ion conductive ceramics (e.g., yttria stabilized zirconia) as a main constituent material thereof is contained in a tubular containment member (casing) made of metal has widely been known. The gas sensor is attached along an exhaust path of the internal combustion engine, and is used to sense the predetermined gas component in the exhaust gas and to measure the concentration thereof.

One end portion of the casing has an opening, and a seal member made of rubber is fit into the opening. A protective cover through which the exhaust gas can enter and exit is attached to the other end portion of the casing. The sensor element is contained in the casing while a portion between the both end portions is sealed to be airtight. This allows one end portion of the sensor element to be in contact with a reference gas (typically, ambient air) in the casing on a side of the one end portion of the casing, and allows the other end portion of the sensor element to be exposed in the protective cover to be in contact with the exhaust gas on a side of the other end portion of the casing in the gas sensor. The reference gas and the exhaust gas are not in contact with each other.

The seal member made of rubber is fit into the opening of the casing after a lead for electrically connecting the sensor element to an outside is inserted into a through hole formed in advance, and the fit portion of the casing is swaged from a side part thereof together with the seal member to prevent ingress of water from outside through the opening.

A contact point holding member (connector) made of ceramic including a connection terminal for being electrically connected to the sensor element is disposed in the casing, and the lead lines connected to the connection terminal pass through the seal member to extend outside. In such a case, also already known is a configuration that a member made of ceramic, for example, referred to as a spacer or a separator is disposed between the seal member and the contact point holding member for a purpose of isolation or heat insulation (refer to Japanese Patent No.

6787810, for example). A position of the member such as the spacer is preferably secured so that a member such as an electrode is not broken due to vibration from outside or application of impact, for example.

In a gas sensor disclosed in Japanese Patent No. 6787810, an end portion of a sensor element referred to as a detection element is contained in a contact point holding member referred to as a tip end side separator, and a spacer member referred to as a back end side separator intervenes between a seal member referred to as a block member and the tip end side separator.

A position of the back end side separator in a longitudinal direction (axial direction) is fixed by sandwiching the back end side separator between the block member and the tip end side separator. In the meanwhile, a position of the back end side separator in a direction (radial direction) perpendicular to the axial direction is fixed by forming a convex-concave structure on each of an end surface of the tip end side separator and an end surface of the back end side separator so as to fit each other and fitting those convex-concave portions.

It is not preferable to provide the convex-concave structure for fitting the contact point holding member and the spacer to each other as disclosed in Japanese Patent No. 6787810 by reason that such a structure causes increase in manufacturing cost from a viewpoint that processing is complex and positioning (phase focusing) in assembling needs to be performed.

There is a growing demand for shortening (reducing a length) and downsizing of a gas sensor due to a narrowed component attachment space of the internal combustion engine in recent years. The configuration that the contact point holding member and the spacer having the convex-concave structure are fitted to each other as disclosed in Japanese Patent No. 6787810 is disadvantageous from a viewpoint of shortening and downsizing in both the axial direction and the radial direction in a point that fitting portions need to be ensured.

SUMMARY

The present invention is directed to a gas sensor and, in particular, to securing of a spacer disposed in a casing for containing a sensor element.

According to the present invention, a gas sensor for sensing a predetermined gas component contained in a measurement gas, the gas sensor includes: a sensor element including a sensing part on one end portion thereof; a casing in which the sensor element is contained and secured; and a connector disposed in the casing to electrically connect the sensor element to an outside, wherein the casing includes: an outer tube including a main portion in which a reference gas is included and a sealing portion being an end portion having a smaller diameter than the main portion, another end portion of the sensor element protrudes to the main portion, a rubber seal member fitted into the sealing portion to seal the outer tube, and a ceramic spacer intervening between the seal member and the connector in the outer tube. A predetermined position on a lateral side of the sealing portion is a swaging portion swaged from an outside, and the outer tube is sealed with reduction in a diameter of the seal member in the swaging portion. The spacer includes: a first end surface being flat and having contact with the connector, and a second end surface being flat and having contact with the seal member. The spacer is secured by being sandwiched between the connector and the seal member due to friction force between the spacer and the seal member acting on the second end surface which occurs by that predetermined load acts on the spacer from the seal member in accordance with reduction in the diameter of the seal member in the swaging portion.

According to the invention, in the gas sensor having the configuration that both end surfaces of the spacer are flat, the end surfaces have surface contact with the connector and the seal member, respectively, and the spacer is not constrained from the lateral side, the securement of the spacer by sandwiching with the connector and the seal member is implemented.

It is preferable that when an outer diameter of the seal member in a portion other than the swaging portion is A, an outer diameter of the seal member in the swaging portion is B, a distance from a contact surface of the seal member having contact with the second end surface to the swaging portion is C, a width of the swaging portion is D, k is a proportional constant, and the predetermined load is F, $F=k\cdot(A-B)D/C$ is satisfied, and when a minimum value of the predetermined load for sandwiching and securing the spacer by the connector and the seal member is $F_{min}$, and a value of the predetermined load in a case where a contact point deviation occurring between the connector and the sensor element coincides with a maximum allowable range is $F_{max}$, $F_{min}/k \leq (A-B)D/C \leq F_{max}/k$ is satisfied.

In such a case, the spacer can be stably secured by being sandwiched between the connector and the seal member without occurrence of the contact point deviation exceeding the allowable range between the connector and the sensor element.

Accordingly, the object of the present invention is to provide a gas sensor in which a spacer is stably secured without a complex structure.

These and other objects, features, aspects and advantages of the present invention will become more apparent from the following detailed description of the present invention when taken in conjunction with the accompanying drawings.

BRIEF DESCRIPTION OF THE DRAWINGS

FIG. 2 is a diagram illustrating a contact point deviation distance of the gas sensor 100 in a level 1 to a level 4 as a margin for a contact point deviation allowable distance.

FIG. 3 is a cross-sectional view along a length of a sensor element 10.

DESCRIPTION OF THE PREFERRED EMBODIMENTS

Configuration of Gas Sensor

Figure 1:
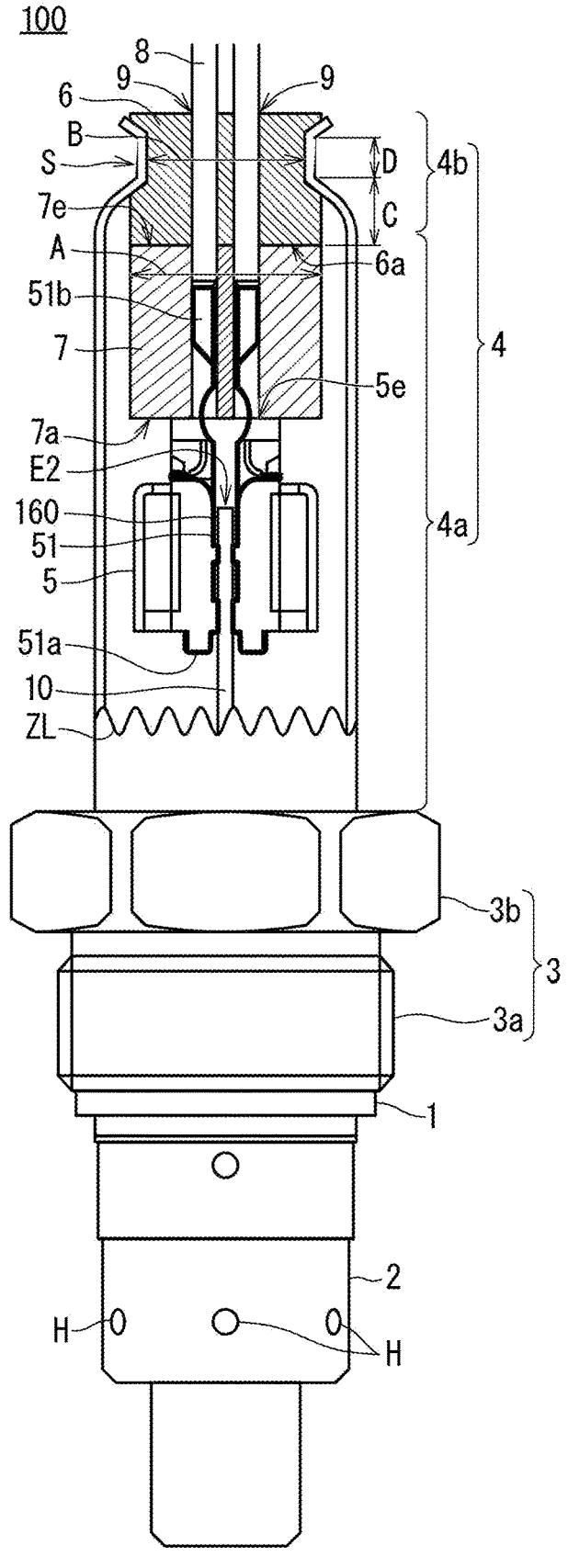
FIG. 1 is a main-part cross-sectional view along a length of a gas sensor 100.

FIG. 1 is a partial cross-sectional view along a length of a gas sensor 100 (more particularly, a main body thereof) according to an embodiment of the present invention. More particularly, a cross-sectional view of the gas sensor 100 is illustrated above a break line ZL, and only appearance of the gas sensor 100 is illustrated below the break line ZL.

The gas sensor 100 is for detecting a predetermined gas component (e.g., NOx) using a sensor element 10 included therein. The gas sensor 100 generally has a configuration in which an elongated columnar or laminar sensor element (detection element) 10 is surrounded by a tubular body 1, a protective cover 2, a securing bolt 3, and an outer tube 4. The tubular body 1, the protective cover 2, and the outer tube 4 as a whole constitute a containment member (casing) for containing the sensor element 10 therein. On the other hand, the securing bolt 3 is fit around an outer side surface of the tubular body 1.

The sensor element 10 is disposed coaxially with the tubular body 1, the protective cover 2, the securing bolt 3, and the outer tube 4. A direction of extension of a central axis of the sensor element 10 is also referred to as an axial direction. In FIG. 1, the axial direction matches an up-down direction in FIG. 1.

More particularly, one end portion (e.g., a first end portion E1 in FIG. 3) of the sensor element 10 is surrounded by the protective cover 2, the other end portion of the sensor element 10 protrudes into the outer tube 4, and a substantially middle portion between the end portions is secured in the tubular body 1 by an unillustrated ceramic green compact or ceramic component while being sealed to be airtight.

The sensor element 10 includes a sensing part (e.g., a gas inlet, an internal chamber, and a sensing electrode) on a side of the one end portion thereof surrounded by the protective cover 2. The sensor element 10 further includes various electrodes and wiring patterns on a surface of and in an element body thereof.

For example, in one aspect of the sensor element 10, a measurement gas introduced into the element is reduced or decomposed in the element to generate oxygen ions. The gas sensor 100 including the sensor element 10 having such a configuration determines the concentration of a gas component to be sensed in the measurement gas based on a quantity of oxygen ions flowing through the element proportional to the concentration of the gas component.

The tubular body 1 is a metal tubular member also referred to as a main metal fitting. The tubular body 1 is barely exposed to an outside of the gas sensor 100, and extends from an upper end portion in FIG. 1 of the protective cover 2 to a lower end portion in FIG. 1 of the outer tube 4. The sensor element 10 and a securing component (the ceramic green compact or the ceramic component) fit around the sensor element 10 are contained in the tubular body 1. In other words, the tubular body 1 is further fit around the fit component, which is fit around the sensor element 10.

The protective cover 2 is a substantially cylindrical exterior member for protecting a predetermined range of the first end portion E1 of the sensor element 10 to be in direct contact with the measurement gas when being in use. The protective cover 2 is secured to a lower end portion in FIG. 1 of the tubular body 1 by welding.

The protective cover 2 has a plurality of through holes H through which gas can pass. The measurement gas flowing into the protective cover 2 through the through holes H is a direct sensing target of the sensor element 10. The types, the numbers, the locations, and the shapes of the through holes illustrated in FIG. 1 are just examples, and may be determined as appropriate in view of flow of measurement gas into the protective cover 2 into consideration.

The securing bolt 3 is an annular member used when the gas sensor 100 is secured to a measurement location. The securing bolt 3 includes a threaded bolt portion 3a and a holding portion 3b held when the bolt portion 3a is engaged. The bolt portion 3a engages with a nut disposed at an attachment location of the gas sensor 100. The gas sensor 100 is thereby secured at the measurement location with a side of the protective cover 2 thereof being in contact with a gas to be measured. For example, the bolt portion 3a engages with a nut portion disposed on an exhaust pipe of a vehicle so that the gas sensor 100 is secured to the exhaust pipe with the side of the protective cover 2 thereof being exposed in the exhaust pipe.

The outer tube 4 is a cylindrical member having one end portion (a lower end portion in FIG. 1) is secured to an outer peripheral end portion of unillustrated upper side of the tubular body 1 by welding. The outer tube 4 includes a main portion 4a extending from a part where the outer tube 4 is secured to the tubular body 1 by welding to have a constant diameter in the axial direction, and a sealing portion 4b contiguous with the main portion 4a in the axial direction. The sealing portion 4b is an end portion having a smaller diameter than the main portion 4a.

An internal space of the outer tube 4 is a reference gas (ambient air) atmosphere. A connector (also referred to as a contact point holding member) 5 and the spacer 7 are disposed in the main portion 4a.

On the other hand, the sealing portion 4b is a portion laterally swaged with the seal member 6 being fit into the sealing portion 4b to seal the other end portion (an upper end portion in FIG. 1) of the outer tube 4.

The outer tube 4 is sealed by swaging an entire circumference of the sealing portion 4b from outside in a swaging portion S lateral to the seal member 6 in FIG. 1 so that the seal member 6 generates radially outward reaction force.

The seal member 6 is made of rubber. Thus, the seal member 6 is also referred to as a rubber plug or a grommet. The rubber to be used is typically fluororubber. The seal member 6 has a uniform cylindrical shape before being fitted into the sealing portion 4b, but is deformed in a radial direction by fitting and swaging. The seal member 6 has contact with the spacer 7 at an end surface 6a in the outer tube 4 (a lower end portion in FIG. 1).

The other end portion (e.g., a second end portion E2 in FIG. 3) of the sensor element 10 is inserted into the connector 5. The connector 5 includes a plurality of contact point members 51 made of metal to be in contact with a plurality of electrode terminals 160 (see FIG. 3) of the sensor element 10 when the sensor element 10 is inserted. One end portion (a lower end portion in FIG. 1) of each of the contact point members 51 is a hooked portion 51a hooked to the connector 5, the other end portion (an upper end portion in FIG. 1) of each of the contact point members 51 is a crimping portion 51b to which a lead 8 is secured by crimping, and a portion between the end portions is a leaf spring portion. The contact point members 51 are secured by being sandwiched between the connector 5 and the sensor element 10, so that the electrode terminals 160 of the sensor element 10 and the contact point members 51 are electrically connected.

The connector 5 has contact with the spacer 7 at an end surface 5e on a side opposite to a side on which the sensor element 10 is inserted (an upper end portion in FIG. 1).

The spacer 7 is sandwiched (intervenes) between the connector 5 and the seal member 6 in the outer tube 4. The spacer 7 is provided to suppress increase in temperature of the seal member 6 in using the gas sensor 100. Ceramics is selected as a material of the spacer 7 from a viewpoint of ensuring strength.

Preferably selected is ceramics having a thermal conductivity of 32 W/m·K or less, which is suitable from a viewpoint of heat insulating properties. More preferably, alumina (thermal conductivity: 32 W/m·K) or steatite (thermal conductivity: 2 W/m·K) is selected.

The spacer 7 has contact with the end surface 5e of the connector 5 at an end surface 7a on a side of one end portion thereof (a lower end portion in FIG. 1), and has contact with the end surface 6a of the seal member 6 at an end surface 7e on a side of the other end portion (an upper end portion in FIG. 1). Both the end surface 7a and the end surface 7e of the spacer 7 are flat except for a through hole 9. Thus, in the gas sensor 100 according to the present embodiment, the spacer 7 is secured by being sandwiched between the connector 5 and the seal member 6 while the connector 5 and the spacer 7 have surface contact with each other, and the seal member 6 and the spacer 7 have surface contact with each other.

Each of leads 8 is inserted into through holes 9 sequentially provided in the seal member 6 and the spacer 7, and has one end portion secured to the crimping portion 51b of the contact point member 51 by crimping and the other end portion connected to a controller 50 and various power supplies (see FIG. 3) outside the gas sensor 100. The sensor element 10 is thereby electrically connected to the controller 50 and the various power supplies through the contact point members 51 and the leads 8. While only two contact point members 51 and two leads 8 are illustrated in FIG. 1, they are for ease of illustration, and the required number of leads for electrical connection described above are actually provided.

The gas sensor 100 having the above configuration can be manufactured by a method similar to a conventional method. Schematically, prior to swaging at the swaging portion S, the connector 5 into which the sensor element 10 has been inserted and in which the contact point members 51 have been connected to the leads 8 is disposed in the main portion 4a of the outer tube 4 in advance. Subsequently, the spacer 7 and the seal member 6 are then stacked on the connector 5 in this order while the leads 8 are inserted into the through holes 9 therein. The seal member 6 into which the leads 8 are inserted is fitted into the sealing portion 4b before swaging. Typically, ambient air as the reference gas has already entered the outer tube 4 before the seal member 6 is fit into sealing portion 4b. The swaging portion S is swaged by a predetermined swaging means after the seal member 6 is fitted.

It is a favorable example to swage the swaging portion S continuously extending over the outer periphery of sealing portion 4b, however, the swaging portion S may discontinuously extend in a circumferential direction of sealing portion 4b as long as a favorable swaging securing is achieved.

Dimension Relationship in Seal Member

As described above, in the gas sensor 100 according to the present embodiment, both the end portion 7a and the end portion 7e of the spacer 7 are flat, and the end portion 7a and the end portion 7e have surface contact with the connector 5 and the seal member 6, respectively. Accordingly, the spacer 7 is secured by being sandwiched between the connector 5 and the seal member 6 in the axial direction (the up-down direction FIG. 1, the same applies to the description hereinafter), but is not constrained from the lateral side (radial direction) at all. However, in the gas sensor 100, the seal member 6 satisfies a predetermined dimension relationship in securing by swaging described above, thus a stable securing state of the spacer 7 is achieved in not only the axial direction but also the radial direction perpendicular to the axial direction.

Schematically, this is achieved by using (static) friction force occurring between the seal member 6 and the spacer 7 in the radial direction. The friction force occurs as a result that the seal member 6 generates reaction force toward an outer side in the radial direction due to the swaging of the swaging portion S by a predetermined swaging means in a process of assembling the gas sensor 100 described above and is to be elongated and deformed in the axial direction, thereby to apply the load to the spacer 7 in the axial direction so that the spacer 7 is pressed against the connector 5. The friction force is proportional to a predetermined friction coefficient and the axial direction load acting on the spacer 7.

In the gas sensor 100 according to the present embodiment, the swaging portion S is swaged in a manner that the friction force described above preferably acts between the seal member 6 and the spacer 7, thus the movement of the spacer 7 in the radial direction is suppressed even when external force acts on the spacer 7 due to vibration, despite that both the end surfaces 7a and 7e are flat and the spacer 7 and the connector 5 are not bound to each other. That is to say, the spacer 7 is stably secured in the radial direction.

It is preferable that dimensions A, B, C, and D (unit: mm) in four positions in FIG. 1 described hereinafter satisfy a predetermined relationship to stably achieve the state where the spacer 7 is secured.

A: an outer diameter of the seal member 6 other than the swaging portion S (or before swaging);

B: an outer diameter of the seal member 6 in the swaging portion S (after swaging);

C: a distance from the end surface 6a to the swaging portion S (referred to as a swaging pitch hereinafter); and D: a width of the swaging portion S (referred to as a swaging length hereinafter).

Firstly, when the axial direction load acting on the spacer 7 from the seal member 6 in swaging is F, the axial direction load F is considered to be proportional to a depth of swaging (a difference of the outer diameter of the seal member 6 before and after swaging) A–B and the swaging length D and is inversely proportional to a pitch C. Thus, the following relational expression is established:

$$F = k \cdot (A-B)D/C \tag{1}$$

Herein, a proportional constant k is a value determined according to materials of the seal member 6 and the spacer 7.

The value of the proportional constant k can be obtained by Expression (1) when both values of the four dimensions A, B, C, and D of the gas sensor 100 and the value of the axial direction load F in the gas sensor are already known.

As for the axial direction load F, there exists a range appropriate to secure the spacer 7. That is to say, the following expression is satisfied:

$$F_{min} \leq F \leq F_{max} \tag{2}$$

$F_{min}$, a minimum value of the axial direction load F (minimum axial direction load) in Expression (2), is a minimum magnitude of the axial direction load F determined to be required to generate the friction force for achieving the stable securing of the spacer 7, on a premise of preferably performing swaging of the seal member 6.

In the meanwhile, $F_{max}$, a maximum value of the axial direction load F (maximum axial direction load), is a magnitude of the axial direction load F when a distance (referred to as a contact point deviation distance) of a positional deviation for the contact point member 51 of the connector 5 with respect to an electrode terminal 160 of the sensor element 10 (referred to as a contact point deviation hereinafter) coincides with a maximum allowable distance (a contact point deviation allowable distance) which has been previously set. The deviation may occur in the longitudinal direction of the sensor element 10 caused by the spacer 7, which has received the axial direction load F from the seal member 6, making downward force in FIG. 1 act on the connector 5. When the axial direction load F is excessively large to exceed the maximum axial direction load $F_{max}$, the contact state between contact point member 51 of the connector 5 and the electrode terminal 160 of the sensor element 10 is no longer maintained due to force acting on the connector 5 from the spacer 7 in swaging, thus the axial direction load F needs to be equal to or smaller than the maximum axial direction load $F_{max}$.

When Expression (1) is assigned to Expression (2), the following expression is satisfied:

$$F_{min}/k \leq (A-B)D/C \leq F_{max}/k \tag{3}$$

Expression (3) is a relational expression which is desired to be satisfied by the dimensions A, B, C, and D in four positions in achieving the stable securing of the spacer 7.

Described next is a specific setting of a range indicated by Expression (3) by specifying the proportional constant k, the minimum axial direction load $F_{min}$, and the maximum axial direction load $F_{max}$.

The minimum axial direction load $F_{min}$, is assumed to be 10 (N) based on a result of a preliminary experiment previously performed to specify a relationship between the magnitude of the axial direction load F and the quality of the securing of the spacer 7.

Next, identification of the proportional constant k is described. Table 1 shows a list of the values of four dimensions A, B, C, and D in a case where a combination of the values of the dimensions A, B, C, and D are changed in four levels (a level 1 to a level 4), values of (A–B)D/C calculated based on those values, and a result of determination whether or not the contact point deviation occurs in the gas sensor 100 corresponding to each level. Twelve gas sensors 100 were prepared in the level 1, ten gas sensors 100 were prepared in each of the level 2 and the level 3, and five gas sensors 100 were prepared in the level 4 to confirm whether or not the contact point deviation occurred in each level.

TABLE 1

|  | A | B | C | D | (A − B)D/C | Contact point deviation |
|---|---|---|---|---|---|---|
| Level 1 | 11 | 9.4 | 2.3 | 4.4 | 3.06 | Present |
| Level 2 | 11 | 9.4 | 2.3 | 2.4 | 1.67 | None |
| Level 3 | 11 | 9.4 | 4.3 | 2.4 | 0.89 | None |
| Level 4 | 11 | 9.4 | 6.3 | 2.4 | 0.61 | None |

It is confirmed by the preliminary experiment which has been previously performed that the axial direction load in the gas sensor 100 of the level 2 is 150 (N). Then, in accordance with Table 1 and Expression (1), the following expression is satisfied:

$$F = k \cdot 1.67 \text{ (mm)} = 150 \text{ (N)}$$

Thus, the value of the proportional constant k is obtained as:

$$k = 150/1.67 = 89.8 \text{ (N/mm)}$$

Then, the following relational expression is established by Expression (3).

$$F_{min}/89.8 \leq (A-B)D/C \leq F_{max}/89.8 \tag{3a}$$

In the meanwhile, the maximum axial direction load $F_{max}$ is the value which can be set based on the result of the preliminary experiment considering a margin (unit: %) for the contact point deviation allowable distance which has been previously set.

FIG. 2 is a diagram illustrating a contact point deviation distance of the gas sensor 100 in the level 1 to the level 4 shown in Table 1 as the margin for the contact deviation allowable distance.

The margin of the contact point deviation distance for the contact point deviation allowable distance is expressed by the following expression.

$$\text{Margin (\%)}=100\times(1-\text{contact point deviation distance/contact point deviation allowable distance}) \quad (4)$$

In accordance with Expression (4), a state where the margin is 100% indicates that no contact point deviation occurs, a state where the margin is 0% indicates that the contact point deviation distance coincides with the contact point deviation allowable distance, and a state where the margin is negative indicates that the contact point deviation distance exceeds the contact point deviation allowable distance.

Confirmed from FIG. 2 and Table 1 is that the contact point deviation exceeding the contact point deviation allowable distance occurs in almost all of the gas sensors 100 in the level 1, however, the contact point deviation exceeding the contact point deviation allowable distance does not occur in the gas sensor 100 in the level 2 to the level 4. However, it is confirmed that the margin is almost 100% and the contact point deviation does not substantially occur in the gas sensor 100 in the level 4, and on the other hand, some gas sensor 100 in the level 2 has the margin of 0%.

In light of the above results, in the present embodiment, a value slightly smaller than the axial direction load F acting on the spacer 7 in the gas sensor 100 in the level 2 is set as the maximum axial direction load $F_{max}$. Specifically, the maximum axial direction load is set to 148 (N).

In such a case, the following relational expression is introduced by assigning the values of $F_{min}$ and $F_{max}$ to Expression (3a).

$$10/89.8 \le (A-B)D/C \le 148/89.8$$

$$0.11 \le (A-B)D/C \le 1.65 \quad (5)$$

Expression (5) is nothing less than a specific relational expression of Expression (3).

As described above, according to the present embodiment, in the gas sensor having the configuration that both end surfaces of the spacer are flat, the end surfaces have surface contact with the connector and the seal member, respectively, and the spacer is not constrained from the lateral side, the securement of the spacer by sandwiching with the connector and the seal member is implemented.

Furthermore, the dimensions A, B, C, and D of four positions regarding the seal member satisfy Expression (3) and further Expression (5), thus the spacer can be stably sandwiched and secured without occurrence of the contact point deviation exceeding the allowable range between the connector and the sensor element. The spacer is stably secured without a complex structure such that the spacer and the connector are fitted to each other.

A value of a ratio S1/S2 between the area S1 of the end surface 6a of the seal member 6 and the area S2 of end surface 7e of the spacer 7 having contact with the end surface 6 a is preferably within a range of 0.9 to 1.1 to preferably and stably sandwiching and securing the spacer. When the ratio S1/S2 is smaller than 0.9, the seal member 6 is deformed to escape to an outer side of the spacer 7 in swaging, and significantly appears is that the axial direction load is weakened and friction force decreases, thus such a ratio is not preferable. A configuration that the ratio S1/S2 exceeds 1.1 requires to increase the diameter of the outer tube 4 and increase the size of the gas sensor 100, thus such a ratio is not preferable.

Example of Configuration of Sensor Element

A configuration of the sensor element 10 for detecting NOx as an example of the sensor element 10 will finally be described. FIG. 3 is a cross-sectional view along the length of the sensor element 10 for detecting NOx. In this case, the sensor element 10 is a so-called limiting current type gas sensor element. FIG. 3 illustrates a pump cell power supply 30, a heater power supply 40, and the controller 50 of the gas sensor 100 in addition to the sensor element 10.

As illustrated in FIG. 3, the sensor element 10 generally has a configuration that a portion of an elongated planar element base 11 on the side of the first end portion E1 is covered with a porous leading-end protective layer 12. The element base 11 includes an elongated planar ceramic body 101 as a main structure, and main-surface protective layers 170 (170a and 170b) are arranged on two main surfaces of the ceramic body 101. Furthermore, in the sensor element 10, the leading-end protective layer 12 (an inner leading-end protective layer 12a and an outer leading-end protective layer 12b) is disposed outside an end surface (a leading end surface 101e of the ceramic body 101) and four side surfaces on a side of one leading end portion.

In the present embodiment, end portions of the ceramic body 101 and the sensor element 10 on the side of the first end portion E1 of the element base 11 are also referred to as first end portions E1 and end portions of the ceramic body 101 and the sensor element 10 on a side of the second end portion E2 of the element base 11 are also referred to as second end portions E2 for the sake of convenience.

The ceramic body 101 is made of ceramics including, as a main component, zirconia (yttrium stabilized zirconia), which is an oxygen-ion conductive solid electrolyte. The ceramic body 101 is dense and airtight.

The sensor element 10 illustrated in FIG. 3 is a so-called serial three-chamber structure type gas sensor element including a first internal chamber 102, a second internal chamber 103, and a third internal chamber 104 inside the ceramic body 101. That is to say, in the sensor element 10, the first internal chamber 102 communicates, through a first diffusion control part 110 and a second diffusion control part 120, with a gas inlet 105 opening to the outside on the side of the first end portion E1 of the ceramic body 101 (to be precise, communicating with the outside through the leading-end protective layer 12), the second internal chamber 103 communicates with the first internal chamber 102 through a third diffusion control part 130, and the third internal chamber 104 communicates with the second internal chamber 103 through a fourth diffusion control part 140, in outline. A path from the gas inlet 105 to the third internal chamber 104 is also referred to as a gas distribution part. In the sensor element 10 according to the present embodiment, the distribution part is provided straight along the longitudinal of the ceramic body 101.

The first diffusion control part 110, the second diffusion control part 120, the third diffusion control part 130, and the fourth diffusion control part 140 are each provided as two slits vertically arranged in FIG. 3. The first diffusion control part 110, the second diffusion control part 120, the third diffusion control part 130, and the fourth diffusion control part 140 provide predetermined diffusion resistance to the measurement gas passing therethrough. A buffer space 115 having an effect of buffering pulsation of the measurement gas is provided between the first diffusion control part 110 and the second diffusion control part 120.

An outer pump electrode 141 is provided on an outer surface of the ceramic body 101, and an inner pump electrode 142 is provided in the first internal chamber 102. Furthermore, an auxiliary pump electrode 143 is provided in the second internal chamber 103, and a measurement electrode 145 as the sensing part for directly sensing a gas component to be measured is provided in the third internal chamber 104. In addition, a reference gas inlet 106 which communicates with the outside and through which the reference gas is introduced is provided on the side of the second end portion E2 of the ceramic body 101, and a reference electrode 147 is provided in the reference gas inlet 106.

In the gas sensor 100 including the sensor element 10, the concentration of a NOx gas in the measurement gas is calculated by a process as described below.

First, the measurement gas flowing into the protective cover 2 through the through holes H and introduced into the first internal chamber 102 through the gas inlet 105 is adjusted to have an approximately constant oxygen concentration by a pumping action (pumping in or out of oxygen) of a main pump cell P1, and then introduced into the second internal chamber 103. The main pump cell P1 is an electrochemical pump cell including the outer pump electrode 141, the inner pump electrode 142, and a ceramic layer 101_a_ that is a portion of the ceramic body 101 present between these electrodes. In the second internal chamber 103, oxygen in the measurement gas is pumped out of the element by a pumping action of an auxiliary pump cell P2, which is also an electrochemical pump cell, so that the measurement gas is in a sufficiently low oxygen partial pressure state. The auxiliary pump cell P2 includes the outer pump electrode 141, the auxiliary pump electrode 143, and a ceramic layer 101_b_ that is a portion of the ceramic body 101 present between these electrodes.

The outer pump electrode 141, the inner pump electrode 142, and the auxiliary pump electrode 143 are each formed as a porous cermet electrode (e.g., a cermet electrode made of $ZrO_2$ and Pt that includes Au of 1%). The inner pump electrode 142 and the auxiliary pump electrode 143 to be in contact with the measurement gas are each formed using a material having weakened or no reducing ability with respect to a NOx component in the measurement gas.

NOx in the measurement gas caused by the auxiliary pump cell P2 to be in the low oxygen partial pressure state is introduced into the third internal chamber 104, and reduced or decomposed by the measurement electrode 145 provided in the third internal chamber 104. The measurement electrode 145 is a porous cermet electrode also functioning as a NOx reduction catalyst that reduces NOx present in an atmosphere in the third internal chamber 104. During the reduction or decomposition, a potential difference between the measurement electrode 145 and the reference electrode 147 is maintained constant. Oxygen ions generated by the above-mentioned reduction or decomposition are pumped out of the element by a measurement pump cell P3. The measurement pump cell P3 includes the outer pump electrode 141, the measurement electrode 145, and a ceramic layer 101_c_ that is a portion of the ceramic body 101 existing between these electrodes. The measurement pump cell P3 is an electrochemical pump cell pumping out oxygen generated by decomposition of NOx in an atmosphere around the measurement electrode 145.

Pumping (pumping in or out of oxygen) of the main pump cell P1, the auxiliary pump cell P2, and the measurement pump cell P3 is achieved, under control performed by the controller 50, by the pump cell power supply (variable power supply) 30 applying voltage necessary for pumping across electrodes included in each of the pump cells. In a case of the measurement pump cell P3, a voltage is applied across the outer pump electrode 141 and the measurement electrode 145 so that the potential difference between the measurement electrode 145 and the reference electrode 147 is maintained at a predetermined value. The pump cell power supply 30 is typically provided for each pump cell.

The controller 50 detects a pump current Ip2 flowing between the measurement electrode 145 and the outer pump electrode 141 in accordance with the amount of oxygen pumped out by the measurement pump cell P3, and calculates a NOx concentration in the measurement gas based on a linear relationship between a current value (NOx signal) of the pump current Ip2 and the concentration of decomposed NOx.

The gas sensor 100 preferably includes a plurality of unillustrated electrochemical sensor cells sensing the potential difference between each pump electrode and the reference electrode 147, and each pump cell is controlled by the controller 50 based on a detected signal in each sensor cell.

In the sensor element 10, the heater 150 is buried in the ceramic body 101. The heater 150 is provided, below the gas distribution part in FIG. 3, over a range from the vicinity of the first end portion E1 to at least a location of formation of the measurement electrode 145 and the reference electrode 147. The heater 150 generates heat by being powered from the heater power supply 40 under control performed by the controller 50. The heater 150 is provided mainly to heat the sensor element 10 to enhance oxygen-ion conductivity of the solid electrolyte forming the ceramic body 101 when the sensor element 10 is in use. The sensor element 10 is heated so that the temperature at least in a range from the first internal chamber 102 to the second internal chamber 103 becomes 500° C. or more.

More specifically, the heater 150 is a resistance heating body made, for example, of platinum, and is provided to be surrounded by an insulating layer 151.

The plurality of electrode terminals 160 are formed on the respective main surfaces of the ceramic body 101 on the side of the second end portion E2 to establish electrical connection between the sensor element 10 and the outside. These electrode terminals 160 are electrically connected to the above-mentioned five electrodes, opposite ends of the heater 150, and unillustrated internal wiring for detecting heater resistance through unillustrated internal wiring provided within the ceramic body 101 to have a predetermined correspondence relationship. As described above, the electrode terminals 160 are connected to the leads 8 via the contact point members 51, and application of a voltage from the pump cell power supply 30 to each pump cell of the sensor element 10 and heating using the heater 150 by being powered from the heater power supply 40 are thus performed through the leads 8, the contact point members 51, and the electrode terminals 160.

The main-surface protective layers 170 are layers made of alumina, having a thickness of approximately 5 μm to 30 μm, and including pores with a porosity of approximately 20% to 40%, and are provided to prevent adherence of any foreign matter and poisoning substances to the two main surfaces of the ceramic body 101 and the outer pump electrode 141. The main-surface protective layer 170_a_ thus functions as a pump electrode protective layer for protecting the outer pump electrode 141.

The leading-end protective layer 12 is provided around an outermost periphery of the element base 11 in a predetermined range from the first end portion E1. The leading-end protective layer 12 is provided in a manner of surrounding a portion of the element base 11 in which the temperature is high (up to approximately 700° C. to 800° C.) when the gas sensor 100 is in use, in order to ensure water resistance in the portion to thereby suppress the occurrence of cracking (water-induced breakage) of the element base 11 due to thermal shock caused by local temperature reduction upon direct exposure of the portion to water.

In addition, the leading-end protective layer 12 is also provided to ensure poisoning resistance to prevent poisoning substance such as Mg from entering into the sensor element 10.

The inner leading-end protective layer 12*a* is made of alumina, has a porosity of 45% to 60%, and has a thickness of 450 μm to 650 μm. The outer leading-end protective layer 12*b* is made of alumina, has a porosity of 10% to 40%, which is lower than the porosity of the inner leading-end protective layer 12*a*, and has a thickness of 50 μm to 300 μm. The inner leading-end protective layer 12*a* is provided as a low-thermal conductivity layer to have a function of suppressing thermal conduction from the outside to the element base 11.

The inner leading-end protective layer 12*a* and the outer leading-end protective layer 12*b* are formed by sequentially thermal spraying (plasma-spraying) constituent materials with respect to the element base 11 having a surface on which an underlying layer 13 has been formed.

As illustrated in FIG. 3, the underlying layer 13 is provided between the inner leading-end protective layer 12*a* and the element base 11 to secure an adhesion of the inner leading-end protective layer 12*a*. The underlying layer 13 is provided at least on the two main surfaces of the element base 11. The underlying layer 13 is made of alumina, has a porosity of 30% to 60%, and has a thickness of 15 μm to 50 μm.

Modification

While the limiting current type sensor element having three internal chambers and detecting NOx as a gas component to be detected is shown as an example of the sensor element 10 in the above-mentioned embodiment, the number of internal chambers may not be three and a gas component other than NOx may be detected in the sensor element 10 of the gas sensor 100. Alternatively, the sensor element may be a sensor element having no internal chambers, such as a mixed potential type sensor element.

EXAMPLE

A vibration test was performed on the gas sensor 100 in each of the level 2, the level 3, and the level 4 described above for a purpose of confirming stability in securing the spacer 7. The gas sensor having the axial direction load of 10N or less which is lower than the minimum axial direction load $F_{min}$ was also prepared to perform the vibration test in the similar manner.

Specifically, each gas sensor 100 is fixed on a predetermined test table to perform the test under the following conditions:

Acceleration rate: 40 G;

Sweep frequency: 1000 Hz to 3300 Hz; and Sweep speed: 0.057 oct/min.

In the observation of the gas sensor 100 after the test, it is confirmed that a positional deviation in the radial direction occurred in the spacer 7 in the gas sensor having the axial direction load of 10N or less. In the meanwhile, a positional deviation in the radial direction did not occur in the spacer 7 in the gas sensor 100 in the level 2 in which a value of (A–B)D/C slightly exceeded the range of Expression (5) as well as the gas sensors 100 in the level 3 and the level 4 in which a value of (A–B)D/C was within the range of Expression (5).

The above results indicate that the spacer 7 is stably secured by satisfying at least Expression (5).

While the invention has been shown and described in detail, the foregoing description is in all aspects illustrative and not restrictive. It is therefore understood that numerous modifications and variations can be devised without departing from the scope of the invention.

What is claimed is:

1. A gas sensor for sensing a predetermined gas component contained in a measurement gas, the gas sensor comprising:

a sensor element including a sensing part on a side of one end portion thereof;

a casing in which the sensor element is contained and secured; and a connector disposed in the casing to electrically connect the sensor element to an outside, wherein the casing includes:

an outer tube including a main portion in which a reference gas is included and a sealing portion being an end portion having a smaller diameter than the main portion, another end portion of the sensor element protruding to the main portion, a rubber seal member fitted into the sealing portion to seal the outer tube, and a ceramic spacer intervening between the seal member and the connector in the outer tube, a predetermined position on a lateral side of the sealing portion is a swaging portion swaged from an outside, and the outer tube is sealed with reduction in a diameter of the seal member in the swaging portion, the spacer includes:

a first end surface on a side of one end portion thereof being flat and having contact with the connector, and a second end surface on a side of other end portion thereof being flat and having contact with the seal member, and, the spacer is secured by being sandwiched between the connector and the seal member due to friction force between the spacer and the seal member acting on the second end surface, which occurs by that predetermined load acts on the spacer from the seal member in accordance with reduction in the diameter of the seal member in the swaging portion, wherein when an outer diameter of the seal member in a portion other than the swaging portion is A, an outer diameter of the seal member in the swaging portion is B, a distance from a contact surface of the seal member having contact with the second end surface to the swaging portion is C, a width of the swaging portion is D, k is a proportional constant, and the predetermined load is F, $$F = k \cdot (A - B)D/C \text{ is satisfied, and}$$

when a minimum value of the predetermined load for sandwiching and securing the spacer by the connector and the seal member is $F_{min}$, and a value of the predetermined load in a case where a contact point deviation occurring between the connector and the sensor element coincides with a maximum allowable range is $F_{max}$, $F_{min}/k{\le}(A{-}B)D/C{\le}F_{max}/k$ is satisfied.

2. The gas sensor according to claim 1, wherein $0.11{\le}(A{-}B)D/C{\le}1.65$ is satisfied.

3. The gas sensor according to claim 1, wherein a value of a ratio S1/S2 between an area S1 of a contact surface of the seal member having contact with the spacer and an area S2 of the second end surface of the spacer having contact with the contact surface is within a range of 0.9 to 1.1.

4. The gas sensor according to claim 1, wherein the seal member is made of fluororubber.

5. The gas sensor according to claim 1, wherein a thermal conductivity of the spacer is equal to or smaller than 32 W/m·K.

6. The gas sensor according to claim 2, wherein a value of a ratio S1/S2 between an area S1 of a contact surface of the seal member having contact with the spacer and an area S2 of the second end surface of the spacer having contact with the contact surface is within a range of 0.9 to 1.1.

7. The gas sensor according to claim 2, wherein the seal member is made of fluororubber.

8. The gas sensor according to claim 3, wherein the seal member is made of fluororubber.

9. The gas sensor according to claim 2, wherein a thermal conductivity of the spacer is equal to or smaller than 32 W/m·K.

10. The gas sensor according to claim 3, wherein a thermal conductivity of the spacer is equal to or smaller than 32 W/m·K.

11. A sensor element containment casing for containing a sensor element and a connector while securing the sensor element therein, the sensor element including, on a side of one end portion thereof, a sensing part for sensing a predetermined gas component contained in a measurement gas, the connector electrically connecting the sensor element to an outside, the sensor element containment casing comprising:

an outer tube including a main portion in which a reference gas is included and a sealing portion being an end portion having a smaller diameter than the main portion, another end portion of the sensor element protruding to the main portion, a rubber seal member fitted into the sealing portion to seal the outer tube, and a ceramic spacer intervening between the seal member and the connector in the outer tube, wherein a predetermined position on a lateral side of the sealing portion is a swaging portion swaged from an outside, and the outer tube is sealed with reduction in a diameter of the seal member in the swaging portion, the spacer includes:

a first end surface on a side of one end portion thereof being flat and having contact with the connector, and a second end surface on a side of other end portion thereof being flat and having contact with the seal member, and, the spacer is secured by being sandwiched between the connector and the seal member due to friction force between the spacer and the seal member acting on the second end surface which occurs by that predetermined load acts on the spacer from the seal member in accordance with reduction in the diameter of the seal member in the swaging portion, wherein when an outer diameter of the seal member in a portion other than the swaging portion is A, an outer diameter of the seal member in the swaging portion is B, a distance from a contact surface of the seal member having contact with the second end surface to the swaging portion is C, a width of the swaging portion is D, k is a proportional constant, and the predetermined load is F, $F{=}k{\cdot}(A{-}B)D/C$ is satisfied, and when a minimum value of the predetermined load for sandwiching and securing the spacer by the connector and the seal member is $F_{min}$, and a value of the predetermined load in a case where a contact point deviation occurring between the connector and the sensor element coincides with a maximum allowable range is $F_{max}$, $F_{min}/k{\le}(A{-}B)D/C{\le}F_{max}/k$ is satisfied.

12. The sensor element containment casing according to claim 11, wherein $0.11{\le}(A{-}B)D/C{\le}1.65$ is satisfied.

13. The sensor element containment casing according to claim 11, wherein a value of a ratio S1/S2 between an area S1 of a contact surface of the seal member having contact with the spacer and an area S2 of the second end surface of the spacer having contact with the contact surface is within a range of 0.9 to 1.1.

14. The sensor element containment casing according to claim 11, wherein the seal member is made of fluororubber.

15. The sensor element containment casing according to claim 11, wherein a thermal conductivity of the spacer is equal to or smaller than 32 W/m·K.

\* \* \* \* \*